US011678984B2

(12) United States Patent
Zhou et al.

(10) Patent No.: US 11,678,984 B2
(45) Date of Patent: Jun. 20, 2023

(54) SYSTEM FOR REPAIRING VALVE LEAFLETS IN MINIMALLY INVASIVE SURGERY

(71) Applicant: Beijing Med Zenith Medical Scientific Co., Ltd., Beijing (CN)

(72) Inventors: Qingliang Zhou, Beijing (CN); Danian Ke, Beijing (CN); Jian Meng, Beijing (CN); Yang Li, Beijing (CN); Yuting Yang, Beijing (CN); Gaoxu Dai, Beijing (CN)

(73) Assignee: Beijing Med Zenith Medical Scientific Co., Ltd.

( * ) Notice: Subject to any disclaimer, the term of this patent is extended or adjusted under 35 U.S.C. 154(b) by 556 days.

(21) Appl. No.: 16/852,006

(22) Filed: Apr. 17, 2020

(65) Prior Publication Data

US 2020/0297490 A1    Sep. 24, 2020

Related U.S. Application Data

(63) Continuation-in-part of application No. PCT/CN2018/110684, filed on Oct. 17, 2018.

(30) Foreign Application Priority Data

Oct. 20, 2017 (CN) .......................... 201710985383.6
May 3, 2018 (CN) .......................... 201810414365.7

(51) Int. Cl.
*A61B 17/128* (2006.01)
*A61F 2/24* (2006.01)
(Continued)

(52) U.S. Cl.
CPC .......... *A61F 2/2457* (2013.01); *A61B 17/128* (2013.01); *A61F 2/246* (2013.01);
(Continued)

(58) Field of Classification Search
CPC ...... A61F 2/2457; A61F 2/2463; A61F 2/246; A61F 2/2454; A61F 2220/0008;
(Continued)

(56) References Cited

U.S. PATENT DOCUMENTS 7,485,143 B2    2/2009  Webler
7,749,245 B2    7/2010  Cohn
(Continued)

FOREIGN PATENT DOCUMENTS

CN    101926697    12/2010
CN    106618803    5/2017
(Continued)

*Primary Examiner* — Timothy J Neal
*Assistant Examiner* — Mitchell Brian Hoag
(74) *Attorney, Agent, or Firm* — Van Pelt, Yi & James LLP

(57) ABSTRACT

A system for repairing a valve leaflet in minimally invasive surgery includes: a delivery device comprising: an operating handle; an outer delivery tube coupled to the operating handle; a delivery needle coupled to the operating handle; and a pushing tube coupled to the operating handle. The system further comprises a repair component comprising an anchor and a connection wire. The delivery device is configured to perform, in response to a trigger operation, a linkage release operation that includes actuating the delivery needle and releasing the repair component.

32 Claims, 24 Drawing Sheets

(51) Int. Cl.
  *A61B 17/04* (2006.01)
  *A61F 2/08* (2006.01)
  *A61B 17/00* (2006.01)
(52) U.S. Cl.
  CPC ........ *A61F 2/2466* (2013.01); *A61B 17/0401* (2013.01); *A61B 2017/00243* (2013.01); *A61B 2017/0409* (2013.01); *A61B 2017/0488* (2013.01); *A61F 2/0811* (2013.01); *A61F 2/2454* (2013.01); *A61F 2/2463* (2013.01); *A61F 2220/0008* (2013.01)
(58) Field of Classification Search
  CPC ................ A61F 2/2466; A61F 2/0811; A61B 17/00234; A61B 2017/00243; A61B 2017/0409; A61B 17/0401; A61B 2017/0488; A61B 17/128; A61B 17/10
  See application file for complete search history.

(56) References Cited

U.S. PATENT DOCUMENTS

| | | | |
|---|---|---|---|
| 8,758,393 B2 | 6/2014 | Zentgraf | |
| 8,834,562 B2 | 9/2014 | Chin-Chen | |
| 8,852,213 B2 | 10/2014 | Gammie | |
| 8,926,693 B2 | 1/2015 | Duffy | |
| 9,782,257 B2 | 10/2017 | Duffy | |
| 10,405,979 B2 | 9/2019 | Schaffner | |
| 2002/0129820 A1 | 9/2002 | Ryan | |
| 2005/0038506 A1 | 2/2005 | Webler | |
| 2005/0261759 A1 | 11/2005 | Lambrecht | |
| 2007/0032796 A1* | 2/2007 | Chin-Chen | A61B 17/0057 606/139 |
| 2007/0255390 A1* | 11/2007 | Ducke | A61F 2/95 623/1.11 |
| 2008/0234701 A1 | 9/2008 | Morales | |
| 2009/0157099 A1* | 6/2009 | Surti | A61B 17/0401 606/151 |
| 2009/0326578 A1* | 12/2009 | Ewers | A61B 17/0401 606/213 |
| 2010/0130989 A1* | 5/2010 | Bourque | A61B 17/0482 606/144 |
| 2011/0264199 A1 | 10/2011 | Tran | |
| 2012/0109156 A1* | 5/2012 | Overes | A61B 17/0482 606/139 |
| 2012/0245417 A1 | 9/2012 | Winterberg | |
| 2014/0088646 A1* | 3/2014 | Wales | A61B 17/0401 606/232 |
| 2014/0379002 A1 | 12/2014 | Morris | |
| 2015/0134057 A1 | 5/2015 | Rourke | |
| 2015/0230789 A1* | 8/2015 | Wales | A61B 17/0401 606/144 |
| 2016/0067039 A1 | 3/2016 | Rourke | |
| 2016/0324636 A1* | 11/2016 | Rourke | A61F 2/2442 |
| 2017/0065409 A1 | 3/2017 | Scorsin | |
| 2017/0202669 A1 | 7/2017 | Schaffner | |
| 2017/0258588 A1 | 9/2017 | Zipory | |
| 2017/0290663 A1 | 10/2017 | Erickson | |
| 2018/0071099 A1 | 3/2018 | Alon | |
| 2018/0085112 A1* | 3/2018 | Sorensen | A61B 17/0482 |
| 2018/0214269 A1* | 8/2018 | Wilson | A61F 2/2466 |
| 2019/0298516 A1 | 10/2019 | Siegel | |
| 2019/0328379 A1* | 10/2019 | Bourque | A61B 17/0483 |
| 2020/0214696 A1* | 7/2020 | Harris | A61B 17/0467 |
| 2022/0087682 A1* | 3/2022 | Ferry | A61B 17/1214 |

FOREIGN PATENT DOCUMENTS

| | | |
|---|---|---|
| EP | 1154738 | 4/2010 |
| EP | 2626014 | 8/2013 |
| EP | 2995279 | 3/2016 |
| JP | S62227346 | 10/1987 |
| JP | H07143992 | 6/1995 |
| WO | 2012006161 | 1/2012 |
| WO | 2016192481 | 12/2016 |
| WO | WO-2016192481 A1 * | 12/2016 |
| WO | 2017035381 | 3/2017 |
| WO | 2017059426 | 4/2017 |
| WO | 2017218877 | 12/2017 |
| WO | 2019076325 | 4/2019 |

* cited by examiner

SYSTEM FOR REPAIRING VALVE LEAFLETS IN MINIMALLY INVASIVE SURGERY

CROSS REFERENCE TO OTHER APPLICATIONS

This application is a continuation-in-part of and claims priority to International (PCT) Application No. PCT/CN18/110684 entitled VALVE LEAFLET REPAIR SYSTEM FOR USE IN PERFORMING MINIMALLY INVASIVE SURGERY, filed Oct. 17, 2018 which is incorporated herein by reference for all purposes, which claims priority to China Application No. 201810414365.7 entitled SYSTEM FOR VALVE LEAFLET REPAIR IN MINIMALLY INVASIVE SURGERY, filed May 3, 2018 which is incorporated herein by reference for all purposes and China Application No. 201710985383.6 entitled VALVE LEAFLET RESTORATION SYSTEM FOR MINIMALLY INVASIVE SURGERY, filed Oct. 20, 2017 which is incorporated herein by reference for all purposes.

TECHNICAL FIELD

The present disclosure relates to the technical field of medical instruments, and in particular, to a system for repairing valve leaflets in minimally invasive surgery.

BACKGROUND OF THE INVENTION

A normal heart valve can ensure blood to flow smoothly in one direction, and effectively pump the blood out of a chamber without regurgitation. Many diseases, such as the rheumatic heart disease and endocarditis, bring about valvular lesions, causing damage to the function of the valve, and stenosis and regurgitation are common valvular diseases. The stenosis is caused by the inability of the valve to open completely, resulting in the blockage of blood flow, and thickening of valve leaflets caused by calcification is a common cause of the stenosis. The regurgitation is caused by the inability of the valve leaflet to close completely, resulting in the backflow of blood to the blood pumping chamber, and valve ring expanding, valve leaflet prolapse and valve leaflet movement blockage are main causes of the regurgitation.

The mitral valve and the tricuspid valve are comprised of leaflets attached to the valve rings, these leaflets are supported at free edges thereof by means of chordae tendineae, and the chordae tendineae are attached to an inner wall of the ventricle and the papillary muscles. However, sometimes, when some of the chordae tendineae are loose or ruptured, the valve prolapse occurs, and therefore the seal normally provided between the atrium and the ventricle is damaged, resulting in blood backflow to the atrium during systole.

Traditional treatment such as repairing or replacing the valves requires thoracotomy and cardiopulmonary bypass. Such surgical procedures are highly complex and have high mortality rates. Minimally invasive surgery procedures have been developed to repair the leaflets. Minimally invasive surgery causes a smaller wound to a human body, and is accomplished with the help of modern imaging equipment such as thoracoscopy and laparoscopy.

Many minimally invasive implanted instruments can only be implanted by performing complex steps by means of an operating handle, and how to make it easier and more convenient to perform these steps is a development direction of minimally invasive instruments. Currently, the implantation in minimally invasive valve leaflet repair surgery is still difficult to operate, and the surgery intensity for the patient and difficulty for the surgeon are relatively high.

SUMMARY

In view of this, the present disclosure provides a system for repairing valve leaflets in minimally invasive surgery, which is a system enabling the surgery to be completed on a beating heart and accurately repairing the function of the valve leaflet. The operation is easy, and release and repair operations can be realized by one step, reducing operation difficulty and patient pain in the surgery.

The technical solution used in the present disclosure includes:

A system for repairing a valve leaflet in minimally invasive surgery, comprising: a delivery device comprising: an operating handle; an outer delivery tube coupled to the operating handle; a delivery needle coupled to the operating handle; and a pushing tube coupled to the operating handle; and a repair component comprising an anchor and a connection wire; wherein the delivery device is configured to perform, in response to a trigger operation, a linkage release operation that includes actuating the delivery needle and releasing the repair component.

In some embodiments, the system further comprises a positioning tube fitted outside the outer delivery tube.

In some embodiments, the system further comprises a positioning tube fitted outside the outer delivery tube, wherein the positioning tube is held in place by an outer tube clamp.

In some embodiments, the system further comprises a positioning tube fitted outside the outer delivery tube, and wherein the positioning tube is made of polymer.

In some embodiments, the operating handle comprises: a pull rod, a push member, a handle casing; wherein the pull rod is connected to the pushing tube; the push member is fitted outside the pull rod; the push member is connected to the delivery needle; the handle casing is fitted outside the push member; the handle casing is connected to the outer delivery tube; the outer delivery tube is fitted outside the delivery needle; and the pushing tube is located inside the delivery needle.

In some embodiments, the pull rod and the push member are cooperatively driven by a spring mechanism.

In some embodiments, the repair component is initially stored inside the delivery needle, and in response to the trigger operation, the pushing tube is configured to release the repair component from inside the delivery needle.

In some embodiments, the pull rod is connected with a tubular structure that stops blood leakage.

In some embodiments, the pull rod is connected with a tubular structure that surrounds and protects the connection wire.

In some embodiments, the pull rod is connected with a tubular structure that surrounds and protects the connection wire, and wherein the tubular structure and the connection wire are severed after the repair component is released.

In some embodiments, the system further comprises a spring mechanism that is located between the pull rod and the push member.

In some embodiments, the system further comprises a snapping member inside the push member, wherein the snapping member is configured to restrict the pull rod before the delivery device is triggered.

In some embodiments, the system further comprises a sliding member formed on the handle casing; and a snapping member located in the push member; wherein the pull rod, the sliding member, and the snapping member are configured such that, when the pull rod is pulled out, the sliding member is placed in a release position, and the pull rod is locked by the snapping member.

In some embodiments, the pull rod, the sliding member, and the snapping member are configured such that, in response to the trigger operation, the push member is ejected, and the sliding member and snapping members come into contact to cause the pull rod to be ejected.

In some embodiments, the system further comprises a release button configured to, in response to the trigger operation, cause the push member to be ejected.

In some embodiments, the system further comprises a safety button configured to prevent accidental triggering of a release button.

In some embodiments, the anchor is to be attached to the valve leaflet.

In some embodiments, the anchor is made of a metal or polymer material.

In some embodiments, the connection wire is connected to the anchor, and the connection wire is made of a polymer material.

In some embodiments, the outer delivery tube, the delivery needle, and the pushing tube form a three-layered structure.

In some embodiments, the push member is fitted outside the pull rod, and the handle casing is fitted outside the push member.

In some embodiments, the operating handle is provided with a first tube seat, a second tube seat, and a third tube seat; the pull rod is connected to the first tube seat; the push member is connected to the second tube seat; and the handle casing is connected to the third tube seat.

In some embodiments, one end of the pushing tube is connected to the first tube seat, and the other end of the pushing tube passes through the center of the second tube seat; one end of the delivery needle is connected to the second tube seat, and the other end of the delivery needle passes through the center of the third tube seat; one end of the outer delivery tube is connected to the third tube seat; and the anchor is connected to the connection wire.

In some embodiments, the first tube seat is provided with a first engaging groove, the pushing tube is provided with a first engaging piece, and the first engaging groove fits with the first engaging piece; the second tube seat is provided with a second engaging groove, the delivery needle is provided with a second engaging piece, and the second engaging groove fits with the second engaging piece; and the third tube seat is provided with a third engaging groove, the outer delivery tube is provided with a third engaging piece, and the third engaging groove fits with the third engaging piece.

In some embodiments, the operating handle includes: a first spring mechanism located on the outside of the pull rod and the inside of the push member, configured to drive the pull rod when the delivery device is triggered; and a second spring mechanism located on the outside of the push member and the inside of the handle casing, configured to drive the push member when the device is triggered.

In some embodiments, the pull rod is connected with an evacuation connector.

In some embodiments, the pull rod is connected to a stretching device configured to hold the connection wire under tension.

In some embodiments, the pull rod encloses a tubular structure that surrounds the connection wire; the tubular structure, the connection wire, and the anchor are configured such that, when the tubular structure and the connection wire within the tubular structure are cut, the anchor is disengaged from the delivery device.

In some embodiments, a first set of sliding grooves is formed on the interior of the push member; a first slider is formed on the exterior of the push member; the first set of sliding grooves and the first slider are configured to be adapted and to allow the pull rod to slide.

In some embodiments, the push member is coupled to a housing structure; a snapping member is provided in the housing structure; a spring is provided to one end of the snapping member; and the snapping member is configured to lock or unlock the pull rod under the control of the spring.

In some embodiments, a second set of sliding grooves is formed on the interior of the handle casing; a second slider is formed on the exterior of the push member; the second set of sliding grooves and the second slider are configured to be adapted to each other and to allow the push member to slide.

In some embodiments, the handle casing further includes: a safety button; a spring coupled to the safety button; and wherein the safety button is configured to lock or unlock the release button under action of the spring.

In some embodiments, the handle casing further includes a safety button reset hole, configured to reset the safety button after the safety button is unlocked.

Compared with existing techniques, the system provided in the present disclosure enables the surgery to be completed on a beating heart. The surgery can accurately repair the function of the valve leaflets by means of the navigation function of modern imaging apparatus, such as ultrasonic apparatus, thoracoscopic apparatus, and laparoscopic apparatus; and the release and repair operations can be realized in one step, therefore reducing operation difficulty and patient pain in the surgery, and improving the successful rate of the surgery.

BRIEF DESCRIPTION OF THE DRAWINGS

Various embodiments of the invention are disclosed in the following detailed description and the accompanying drawings.

FIG. 1C is a cross sectional view of the handle portion of the system shown in

FIG. 1A.

DETAILED DESCRIPTION

Figure 1A:
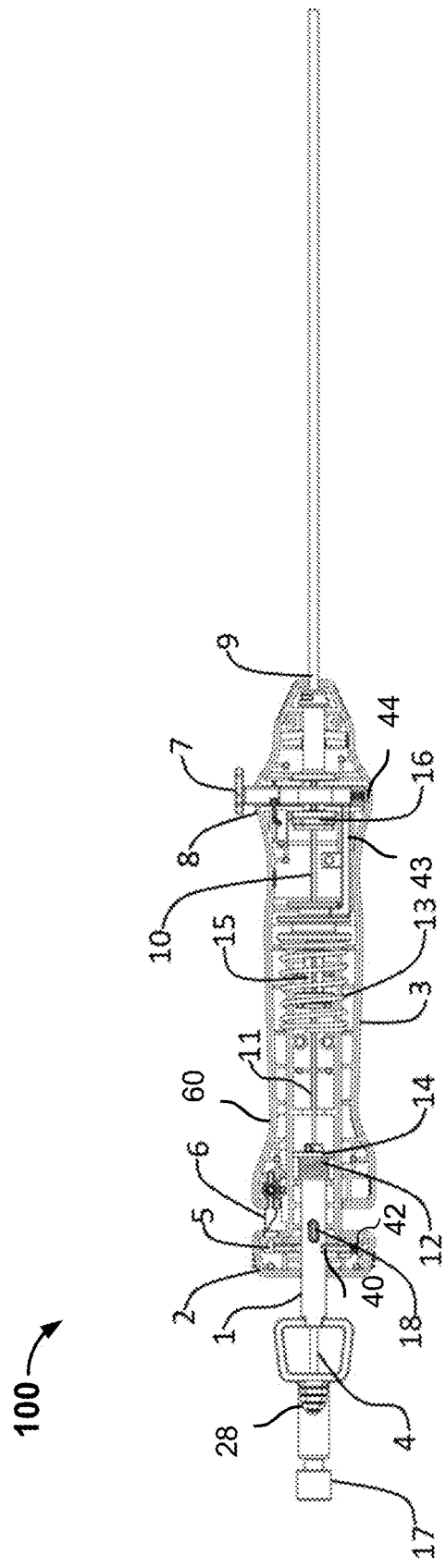
FIG. 1A is a cross sectional view of an embodiment of a valve leaflet repair system before it is triggered.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Hereinafter, specific embodiments of the present disclosure will be described in detail with reference to the accompanying drawings. The numerals used in the drawings represent the following: 1—Pull rod; 2—Push member; 3—Handle; 4—Tubular structure; 5—Snapping member; 6—Sliding member; 7—Release button; 8—Safety button; 9—Outer delivery tube; 10—Delivery needle; 11—Pushing tube; 12—First spring mechanism; 13—Second spring mechanism; 14—First tube seat; 15—Second tube seat; 16—Third tube seat; 17—Evacuation connector; 18—First slider; 19—Positioning tube; 20—Outer tube clamp; 21—Repair component; 22—First engaging groove; 23—Second engaging groove; 24—Third engaging groove; 25—First engaging piece; 26—Second engaging piece; 27—Third engaging piece; 28—Wire clip; 29—Spring; 30—First set of sliding grooves; 31—Second set of sliding grooves; 32—Second slider; 33—Safety button reset hole; 40—Catch; 42—Small spring; 43—L shaped rod; 44—Small spring; 45—Thumb screw; 211—Anchor; 212—Connection wire; 1200—Housing structure.

Figure 13A:
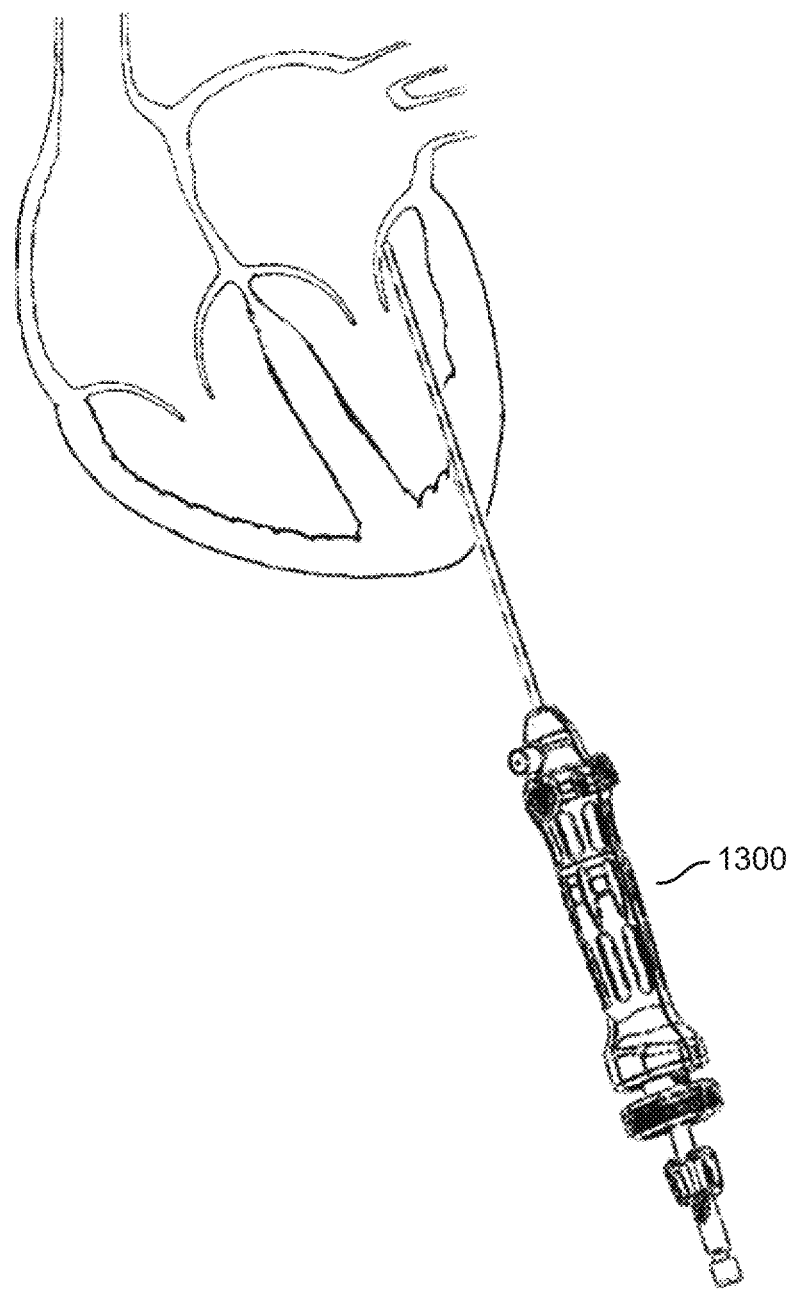
FIGS. 13A-13C are application views of an embodiment of a valve leaflet repair system used in a minimally invasive surgery.
Figure 13B:
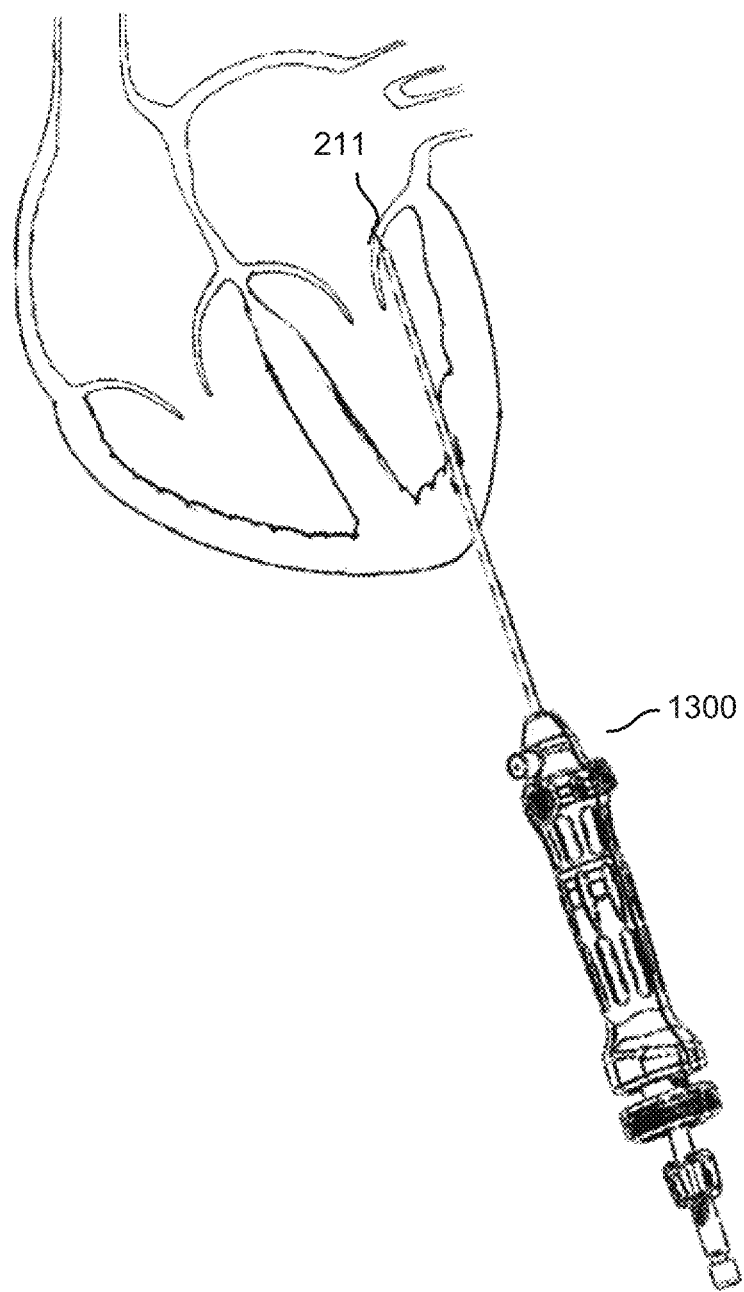
Figure 13C:
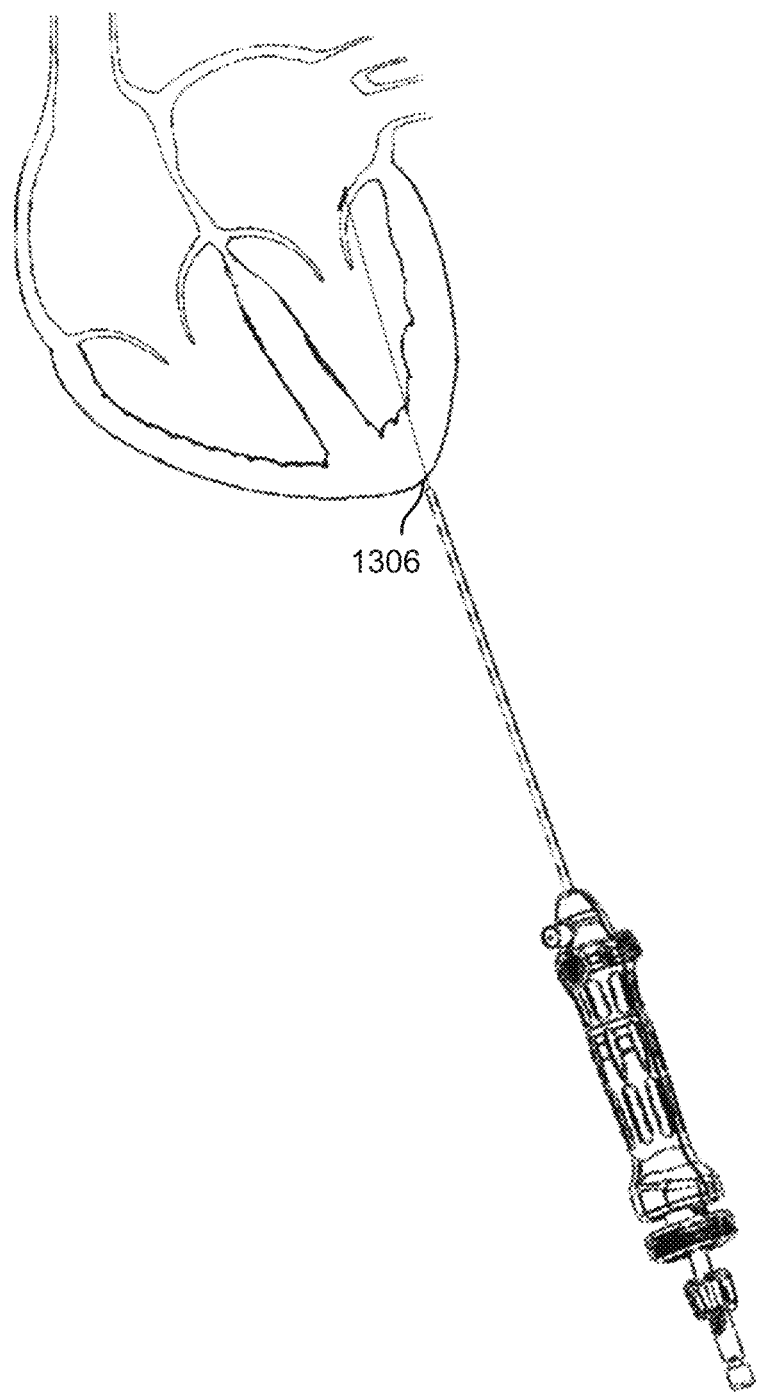

FIGS. 13A-13C are application views of an embodiment of a valve leaflet repair system used in a minimally invasive surgery. System 1300 is configured to deploy, while the heart is beating continuously, a valve repair component (also referred to as a repair component or implant).

As shown in FIG. 13A, a user (e.g., a surgeon) of device 1300 pierces the apex of the heart and places the tip of the device near the diseased valve leaflet, and readies the device for deployment. The surgery is minimally invasive to the heart, as only a small puncture is made to the heart. Although a thoracotomy is still required, the incision to the chest can be much smaller, and no bypass is required. Ultrasound can be used to monitor the movement and operation of the device within the heart chamber.

As shown in FIG. 13B, the surgeon triggers the device. The valve leaflet is pierced, and an anchor 211 that is a part of the valve repair component is ejected and placed on the opposite side of the valve leaflet as the device. The anchor 211 is attached to the device via a connection wire.

As shown in FIG. 13C, the surgeon withdraws the device. The anchor 211 is left at the implant site, still tethered to the connection wire. The connection wire is then cut and tied off at location 1306. The anchor, which is fastened to the valve leaflet, controls the leaflet's position and movement and mitigates the effects of stenosis and regurgitation.

Figure 1B:
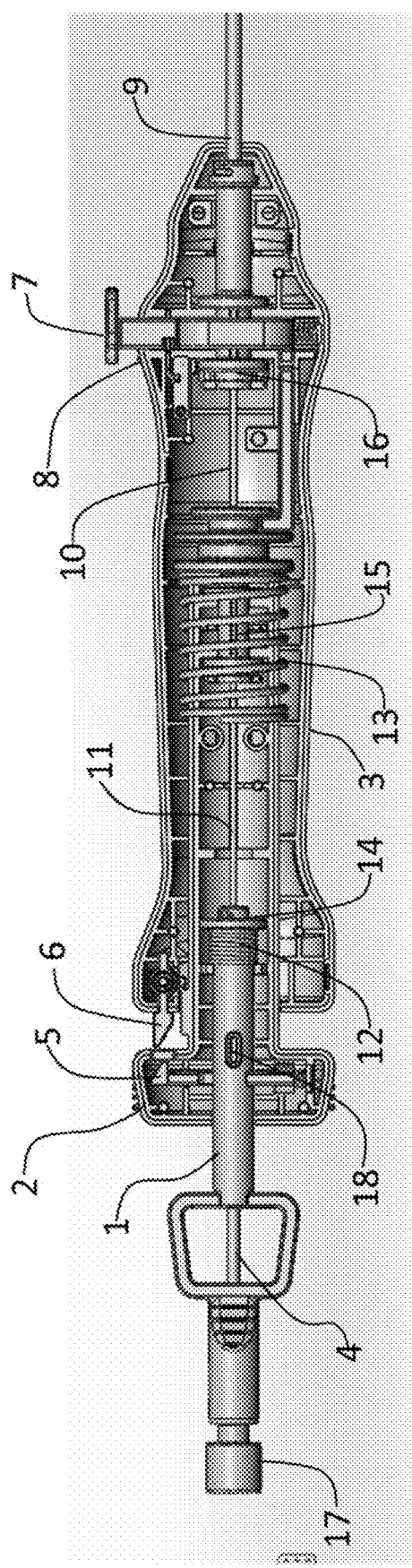
FIG. 1B is a three-dimensional illustration of the system shown in FIG. 1A.
Figure 1C:
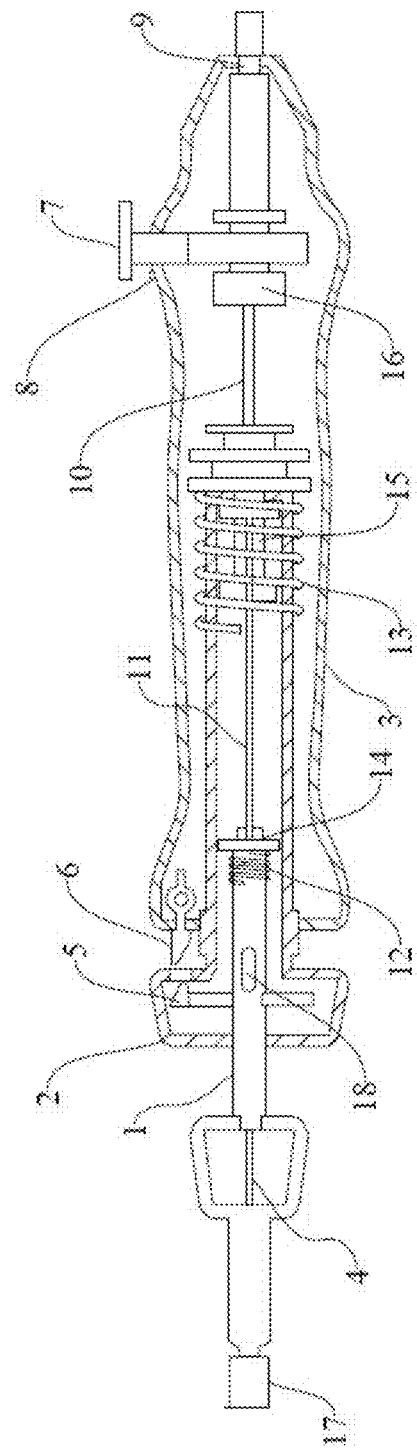

FIG. 1A is a cross sectional view of an embodiment of a valve leaflet repair system before it is triggered. FIG. 1B is a three-dimensional illustration of the system shown in FIG. 1A. FIG. 1C is a cross sectional view of the handle portion of the system shown in FIG. 1A.

Referring to FIGS. 1A-1C, system 100 can be used to implement 1300 of FIGS. 13A-13B. FIGS. 1A-1C illustrate the state of the system prior to being triggered. As shown, the direction from left to right in the figures is referred to as the forward direction.

Figure 3:
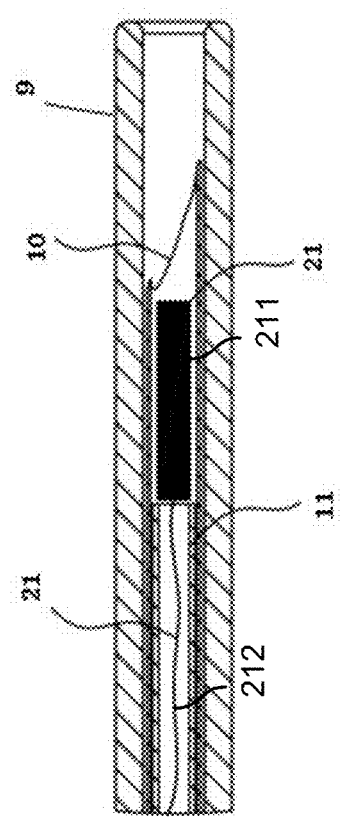
FIG. 3 is a diagram illustrating the front of the operating handle.

System 100 is a delivery device in which the valve repair component is stored initially. The valve repair component is not visible in this figure but greater details are shown in FIG. 3. The delivery device includes an operating handle 60 coupled to an outer delivery tube 9. The repair component (not shown) is stored inside the delivery needle 10, which in turn is stored inside the outer delivery tube 9.

Operating handle 60 includes a pull rod 1, a push member 2, a handle casing 3, a release button 7, a sliding member 6, and an optional safety button 8. Preferably, only after the safety button 8 is activated is the release button 7 unlocked. In various embodiments, the safety button 8 is configured to be activated when it is slid back, pressed down, or in any other appropriate configuration. When the release button 7 is subsequently pressed, the device is triggered. This prevents accidental triggering of the device.

The push member 2 is fitted outside the pull rod 1. The handle casing 3 is fitted outside the push member 2 to house the internal components. A first spring mechanism 12 is fitted on the outside of the pull rod 1 and is located inside the push member 2. When the device is initially configured and before it is triggered, the first spring mechanism 12 is compressed. When the device is triggered, the pull rod 1 cooperates with the push member 2, and is driven by the first spring mechanism 12. In particular, when the device is triggered, the spring mechanism 12 is released, causing the pull rod 1 to move axially relative to the push member 2, in the forward direction.

A second spring mechanism 13 is fitted on the outside of the push member 2. When the device is initially configured and before it is triggered, the second spring mechanism 13 is also compressed. When the device is triggered, the push member 2 cooperates with the handle casing 3, and is driven by the second spring mechanism 13. In particular, when the device is triggered, the spring mechanism 13 is released, causing the push member 2 to move axially relative to the handle casing 3, in the forward direction.

A snapping member 5 is provided in the push member 2. The snapping member 5 is configured to lock or unlock the pull rod 1 under the control of a spring 42 provided to one end of the snapping member 5. When the device is initially configured, the snapping member 5 is configured to restrict the pull rod 1 from ejecting before the device is triggered. In this example, there is a catch 40 on the pull rod 1 that is initially held by the snapping member 5. Under the snapping member 5, a small spring 42 is initially compressed such that a part of snapping member 5 is pushed upward into the catch 40, thus locking the pull rod 1 and restricting its movement. The push member 2 has a sliding groove on the interior that accommodates the pull rod 1 and the first spring mechanism 12. When the device is triggered, the sliding groove allows the sliding of pull rod 1. Further, a slider 32 (not shown in diagram) capable of sliding in the handle casing 3 is formed on the exterior of the push member 2. The handle casing 3 is provided with the sliding member 6. For the initial setup, the push member 2 is pulled out toward the back side of the device, causing the sliding member 6 to automatically slide to a position ready to engage the snapping member 5.

The release button 7 is located at the front end of the handle casing 3, and can move along a set of sliding grooves inside the front end of the handle casing 3. The release button 7 rests on top of a small spring 44. Prior to the device being triggered, the release button 7 locks the push member 2 under the action of the third spring. In this example, an L-shaped rod 43 is pressed against the bottom portion of release button 7 initially, locking push member 2 in place and restricting its movement.

The operating handle is further provided with a first tube seat 14, a second tube seat 15, and a third tube seat 16. The tube seats connect the operating handle to various components of the delivery device, such as the outer delivery tube 9, the delivery needle 10, and the pushing tube 11. The pull rod 1 is coupled to the first tube seat 14. The push member 2 is coupled to the second tube seat 15. One end of the pushing tube 11 is coupled to the first tube seat 14, and the other end of the pushing tube passes through the center of the second tube seat 15. One end of the delivery needle 10 is coupled to the second tube seat 15, and the other end of the delivery needle passes through the center of the third tube seat 16. One end of the outer delivery tube 9 is coupled to the third tube seat 16, and the other end of the outer delivery tube passes through the center of the outer tube clamp 20 and the positioning tube 19 (shown in FIGS. 2A and 2B.)

Figure 1D:
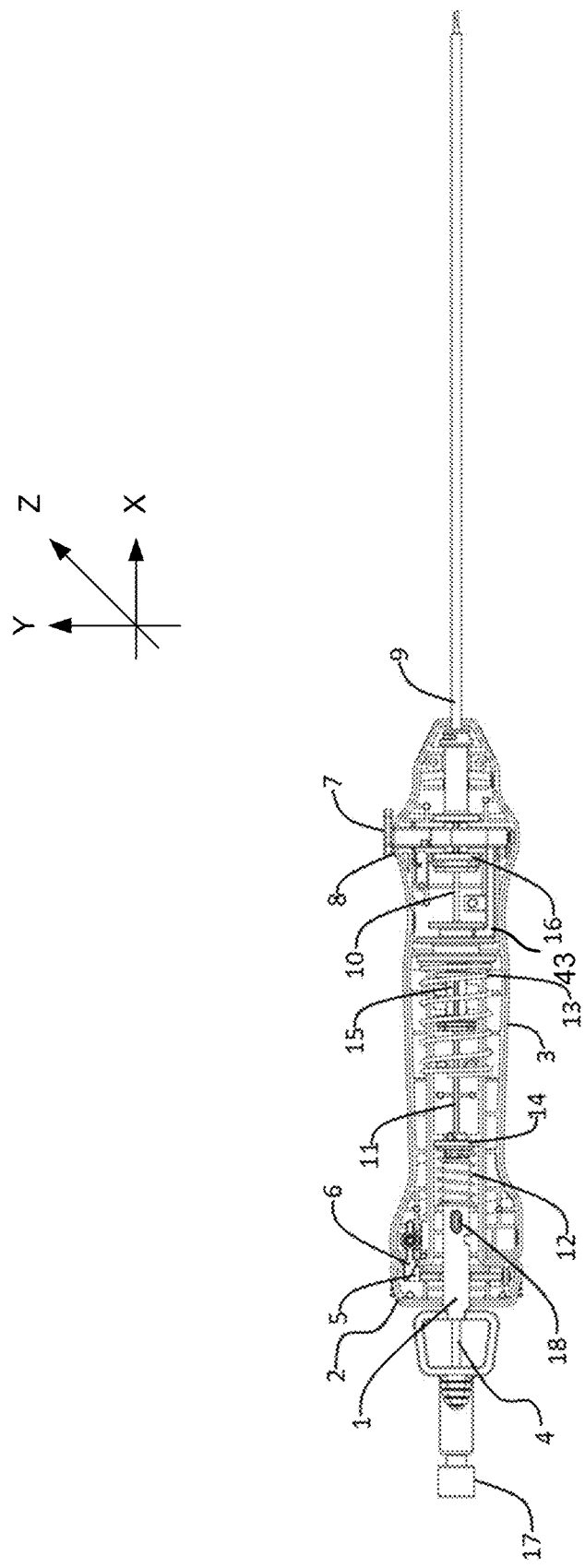
FIG. 1D is a diagram illustrating the state of system 100 after it has been triggered.

FIG. 1D is a diagram illustrating the state of system 100 after it has been triggered. Details of FIG. 1D are explained in further detail below, after the components of the delivery device are described.

Figure 2A:
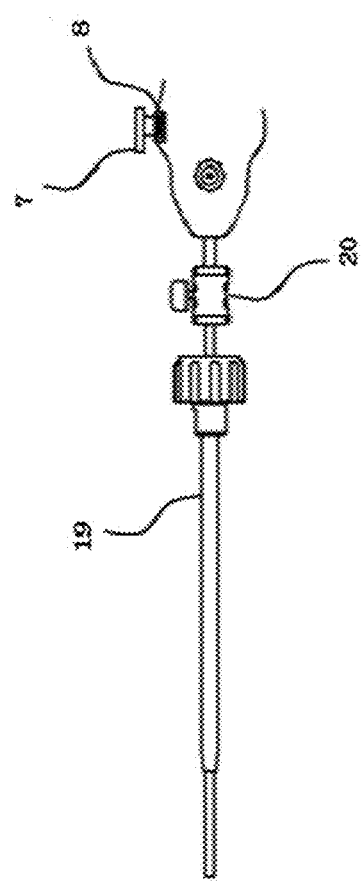
FIG. 2A is a diagram illustrating the front portion of an embodiment of a delivery device that includes optional accessories.

FIG. 2A is a diagram illustrating the front portion of an embodiment of a delivery device that includes optional accessories. In some embodiments, some optional accessories such as a positioning tube and a tube clamp are used. As shown, a positioning tube 19 is fitted outside the outer delivery tube 9. An outer tube clamp 20 holds the positioning tube in place and keeps both the positioning tube 19 and the outer delivery tube 9 in place. In some embodiments, the positioning tube 19 is made of a material such as polymer (e.g., plastic) that is softer than the outer delivery tube. The location of the positioning tube 19 is adjustable. For instance, while moving the device into position for deployment, the surgeon can move the positioning tube 19 such that the tip of the positioning tube 19 is aligned with or extends over the tip of the outer delivery tube 9, thus preventing the hard tip of the outer delivery tube from damaging the tissue during operation. When the surgeon is ready to deploy the device, he or she can move the positioning tube 19 to the position shown in the figure such that the tip of the outer delivery tube 9 is revealed and ready for deployment.

Figure 2B:
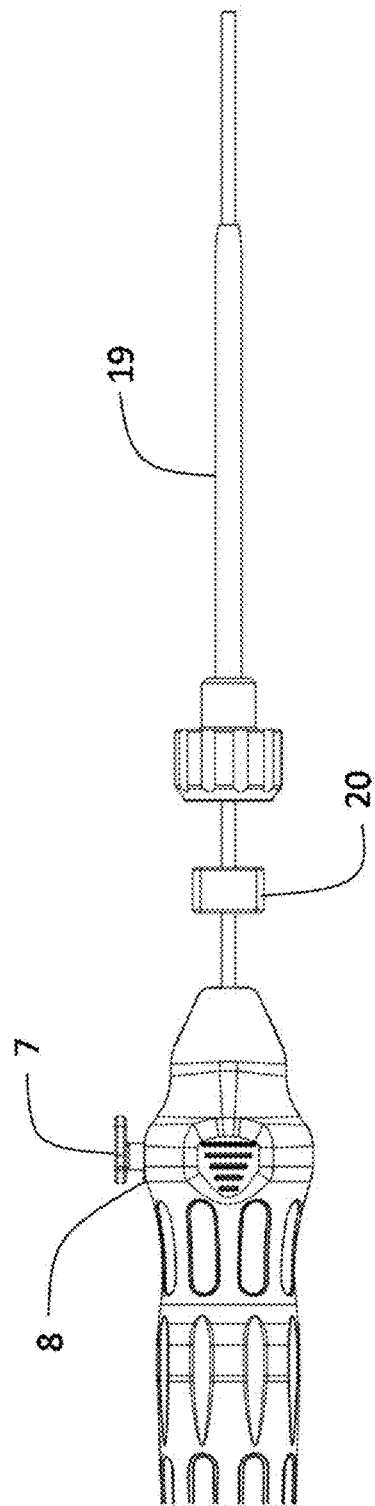
FIG. 2B is another diagram illustrating the front portion of another embodiment of a delivery device.

FIG. 2B is another diagram illustrating the front portion of another embodiment of a delivery device. The diagram is oriented in the same direction as FIG. 1A.

Figure 2C:
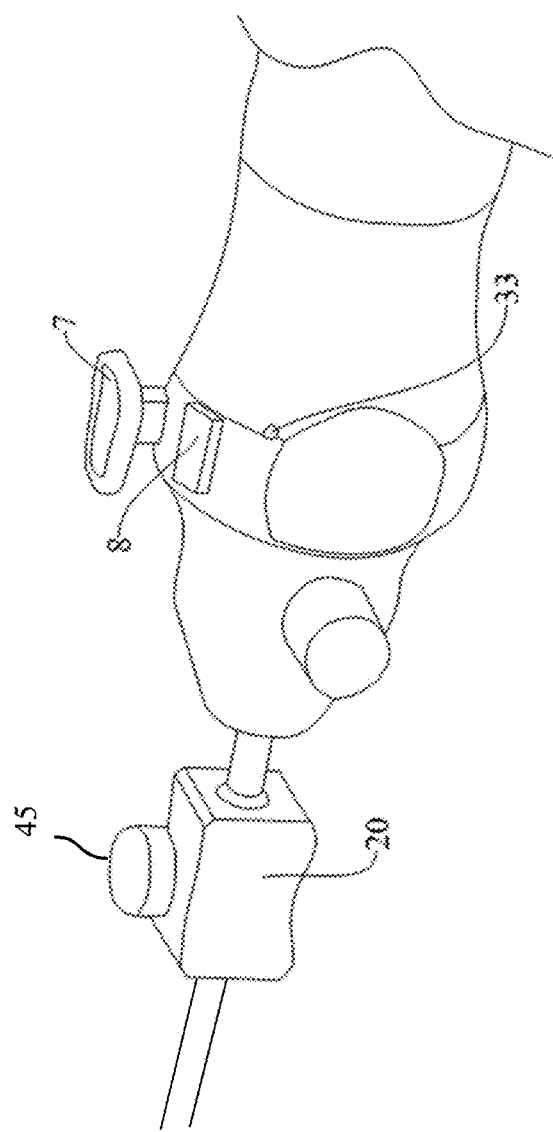
FIG. 2C illustrates the front portion of another embodiment of a delivery device.

FIG. 2C illustrates the front portion of another embodiment of a delivery device. The outer tube clamp 20 is shown in more detail. The outer tube clamp 20 has a thumb screw 45 used to loosen or tighten the positioning tube over the outer delivery tube. In this example, the safety button 8 is provided adjacent to the release button 7. Safety button 8 is used to prevent mis-operations on the release button 7 (e.g., accidental triggering of the release button 7) that can result in the unexpected release of the repair component 21. The safety button 8 is configured to be able to slide along a sliding groove inside the front end of the handle casing 3. The safety button 8 has a locking mechanism (e.g., a catch similar to 40 of FIG. 1A) that initially locks release button 7 to keep it from moving. When safety button 8 is pressed, 7 is unlocked from the locking mechanism (e.g., as the catch moves out of the way) and can be pressed down. A safety button reset hole 33 is provided adjacent to the safety button 8, on the handle casing 3. The safety button reset hole 33 is used for resetting the safety button 8 after the safety button is unlocked (e.g., by resetting the catch to relock the release button 7). After the protection of the safety button is released, when the handle operation needs to be interrupted in the event of an emergency, the safety button can return to the protection state again by resetting the safety button reset hole to relock release button 7.

FIG. 3 is a diagram illustrating the front of the operating handle. As shown, the front of the operating handle is connected to a tube-shaped structure that has multiple layers, including the pushing tube 11, the delivery needle 10, and the outer delivery tube 9. The tubes and needle are preferably made of metal. Other material can be used. The outer delivery tube 9 is fitted outside the delivery needle 10. The delivery needle 10 is hollow, and the pushing tube 11 is placed inside the delivery needle 10 for releasing the repair component by pushing the anchor 211 forward.

The repair component 21 is stored within the delivery needle, and is connected to the delivery device. The repair component 21 includes an anchor 211 and a connection wire 212. The anchor is tied to the connection wire, which is threaded through the hollow inside of the pushing tube 11. Initially, the anchor is provided at an end of the pushing tube 11 and positioned inside the delivery needle 10. The anchor is made of a metal or polymer material. The connection wire is made of polymer material, such as expanded polytetrafluoroethylene or polyester material.

Figure 7:
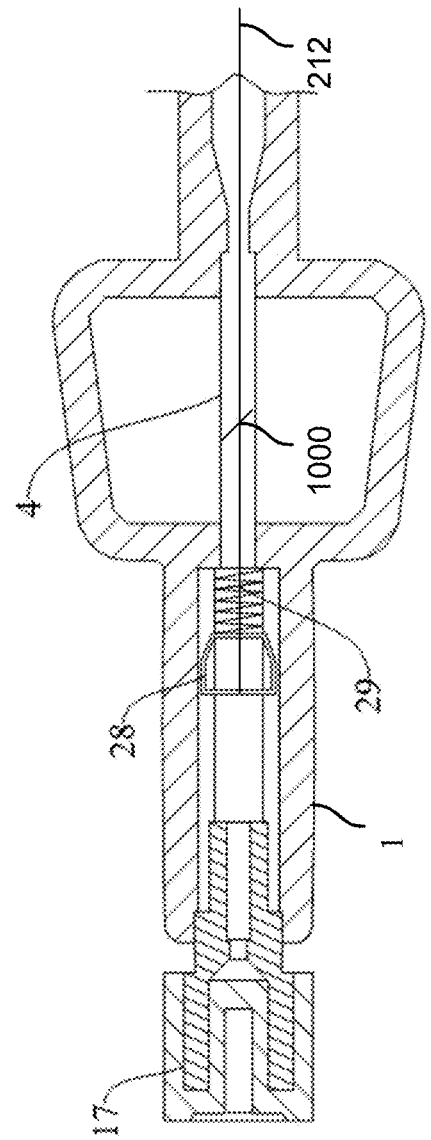
FIG. 7 is a schematic diagram showing the end portion of an embodiment of a device.

Referring to FIG. 7, the connection wire 212 is connected to a wire clip 28 of pull rod 1. Referring again to FIG. 3, in response to a triggering operation (e.g., the surgeon pressing down on the release button 7 after the safety button 8 has been released), the delivery device performs actions such as actuating the delivery needle and releasing the repair component to anchor the valve leaflet. In some embodiments, this is referred to as a linkage release operation because multiple actions are carried out in a single step in response to a single triggering operation, and the user is not required to take multiple steps to cause the individual components to move separately. Specifically, in response to the triggering operation, the second spring mechanism 13 expands, and pushes forward push member 2 and second tube seat 15, which in turn push forward delivery needle 10. When the delivery needle 10 reaches the defective leaflet, the needle will pierce through the leaflet. The pushing tube also pushes the anchor 211 through the pierced hole to the opposite side of the valve leaflet as the device, and continues to push out the anchor from delivery needle 10 to release the anchor. Then the tubular structure and the connection wire within the tubular structure are cut. After the delivery needle is withdrawn, the anchor is placed on the opposite side of the valve leaflet as the device.

As described above, the tube seats are configured to be engaged with the spring mechanisms such that when the spring mechanisms are released, the tube seats and their connected components are pushed forward. FIG. 4A is an exploded view of an embodiment of a first tube seat and a pushing tube. In this embodiment, the first tube seat 14 is made of polymer (e.g., plastic) and the pushing tube 11 is made of metal. Other materials can be used. As shown, the first tube seat 14 is provided with a first engaging groove 22, the pushing tube 11 is provided with a first engaging piece 25, and the first engaging groove 22 fits with the first engaging piece 25.

Figure 4B:
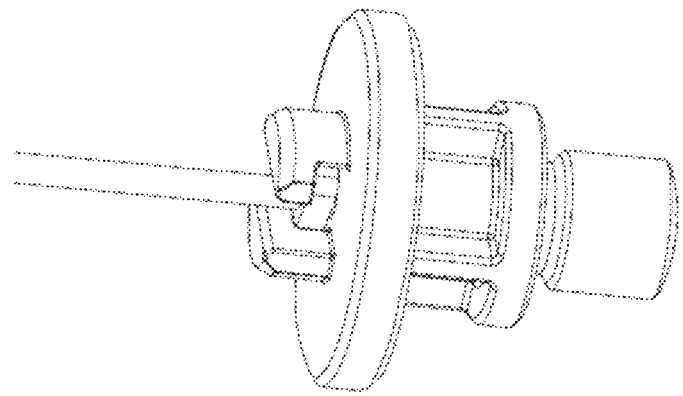
FIG. 4B is an assembled view of an embodiment of a first tube seat and a pushing tube.
Figure 4A:
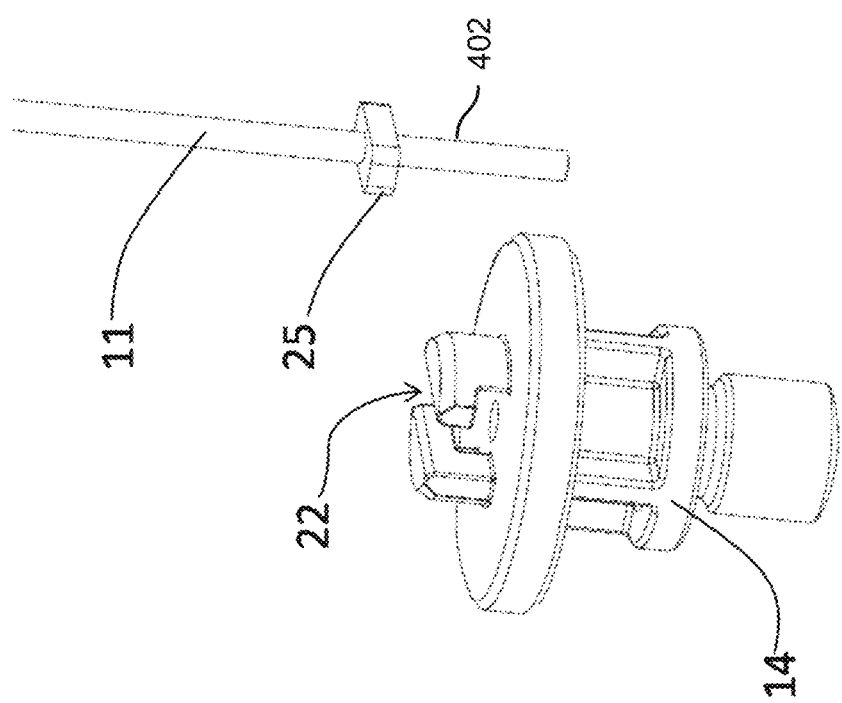
FIG. 4A is an exploded view of an embodiment of a first tube seat and a pushing tube.

FIG. 4B is an assembled view of an embodiment of a first tube seat and a pushing tube. A portion of the pushing tube 11 below the first engaging piece 25 (402 of FIG. 4A) is inserted through the center hole of the first tube seat such that the first engaging groove 22 and the first engaging piece 25 are engaged. In some embodiments, the first tube seat and the pushing tube are adhered by gluing the pieces together.

Figure 5A:
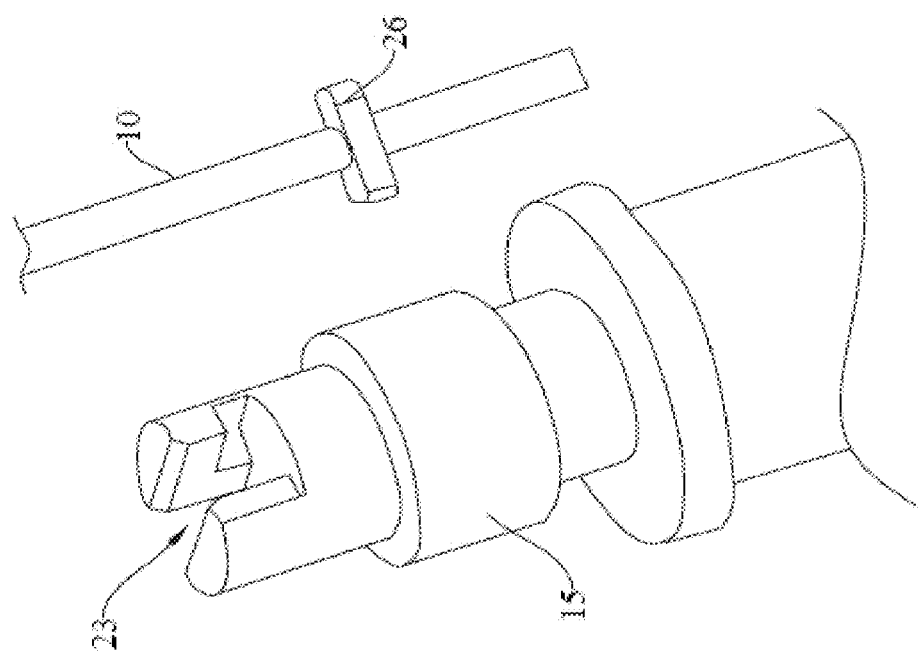
FIG. 5A is an exploded view of an embodiment of a second tube seat and a delivery needle.

FIG. 5A is an exploded view of an embodiment of a second tube seat and a delivery needle. In this embodiment, the second tube seat 15 is made of polymer (e.g., plastic) and the delivery needle 10 is made of metal. Other materials can be used. As shown, the second tube seat 15 is provided with a second engaging groove 23, the delivery needle 10 is provided with a second engaging piece 26, and the second engaging groove 23 fits with the second engaging piece 26. When assembled, a portion of the delivery needle 10 below the second engaging piece 26 is adhered to the second tube seat 15 (e.g., by gluing the second engagement piece 26 to the second tube seat 15).

Figure 5C:
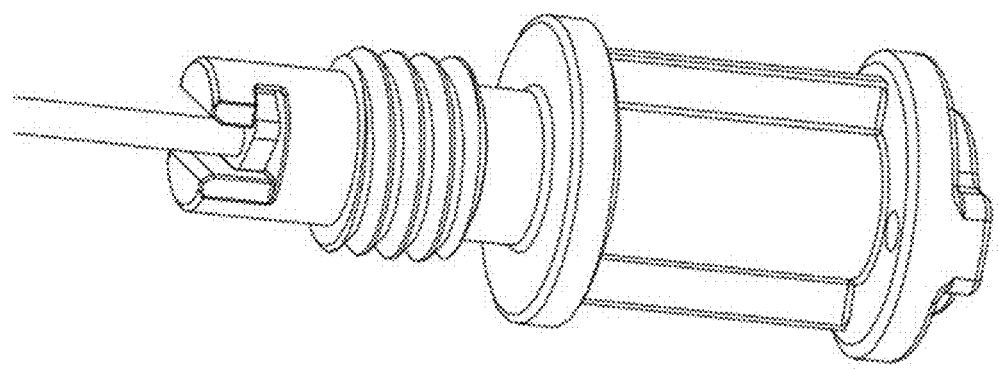
FIG. 5C is an assembled view of an embodiment of a second tube seat and a delivery needle.
Figure 5B:
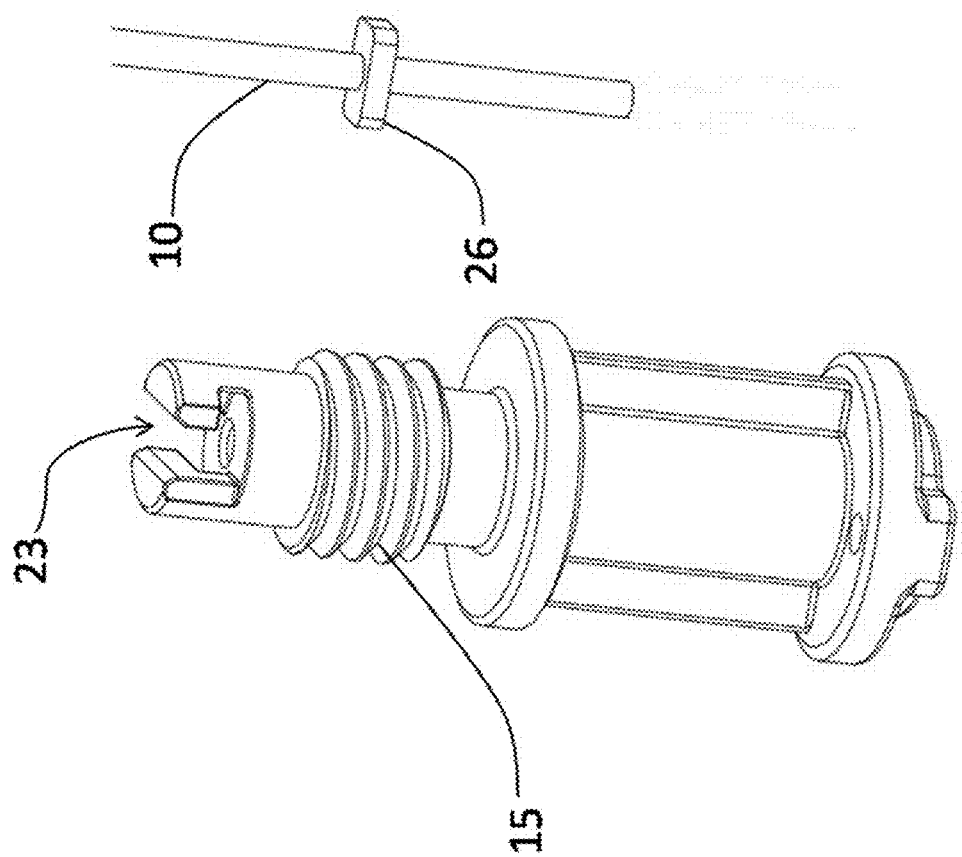
FIG. 5B is an exploded view of another embodiment of a second tube seat and a delivery needle.

FIG. 5B is an exploded view of another embodiment of a second tube seat and a delivery needle.

FIG. 5C is an assembled view of an embodiment of a second tube seat and a delivery needle. As shown, a portion of the delivery needle 10 below the second engaging piece 26 is inserted through the center hole of the second tube seat such that the second engaging groove 23 and the second engaging piece 26 are engaged. The portion of the delivery needle 10 below the second engaging piece 26 is adhered to the second tube seat 15 by gluing the pieces together.

Figure 6B:
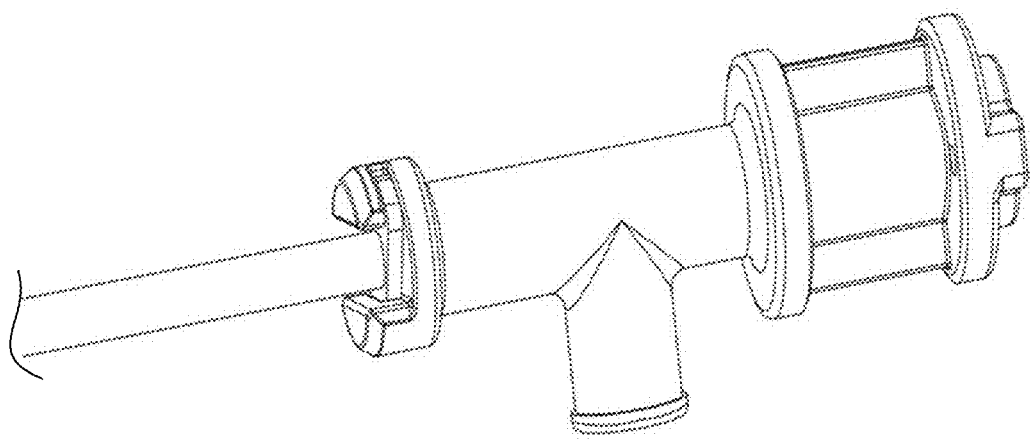
FIG. 6B is an assembled view of an embodiment of a third tube seat and an outer delivery tube.
Figure 6A:
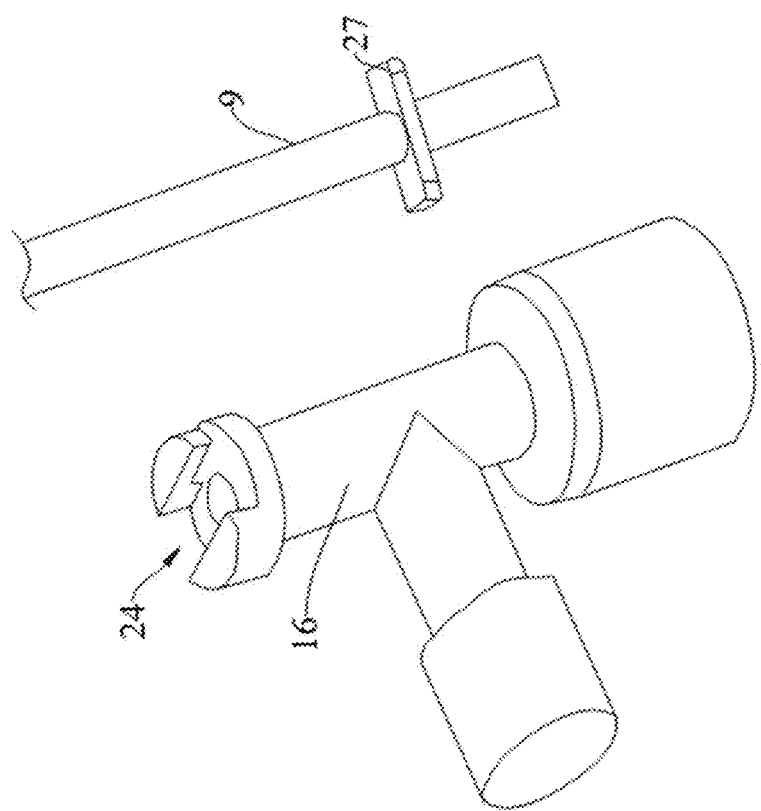
FIG. 6A is an exploded view of an embodiment of a third tube seat and an outer delivery tube.

FIG. 6A is an exploded view of an embodiment of a third tube seat and an outer delivery tube. In this embodiment, the third tube seat 16 is made of polymer (e.g., plastic) and the outer delivery tube 9 is made of metal. Other materials can be used. As shown, the third tube seat 16 is provided with a third engaging groove 24, the outer delivery tube 9 is provided with a third engaging piece 27, and the third engaging groove 24 fits with the third engaging piece 27.

FIG. 6B is an assembled view of an embodiment of a third tube seat and an outer delivery tube. A portion of the outer delivery tube 9 below the third engaging piece 27 is inserted through the center hole of the third tube seat such that the third engaging grove 24 and the third engaging piece 27 are engaged. A portion of the outer delivery tube 9 below the third engaging piece 27 is adhered to the third tube seat 16 by gluing the pieces together.

Glue can seal the tubes and the tube seats, preventing the tubes from rotating and preventing the tubes from disengaging from the tube seats, and the fitting between the engaging pieces and the engaging grooves can prevent the tubes from displacing and disengaging from the tube seats due to impact force during ejection. It should be understood that, in other embodiments, the pushing tube 11, the delivery needle 10 and the outer delivery tube 9 to the respective tube seats may use fastener connections instead of the connection manner of fitting and adhering between engaging pieces and engaging grooves.

Figure 8A:
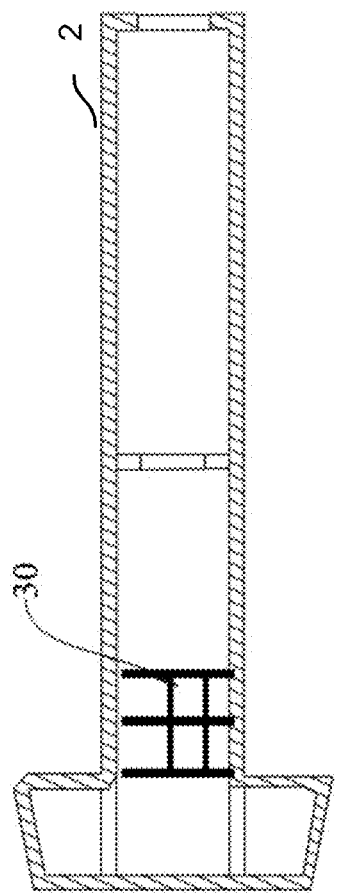
FIG. 8A is a schematic diagram of the interior of an embodiment of a push member with a first set of sliding grooves.
Figure 8B:
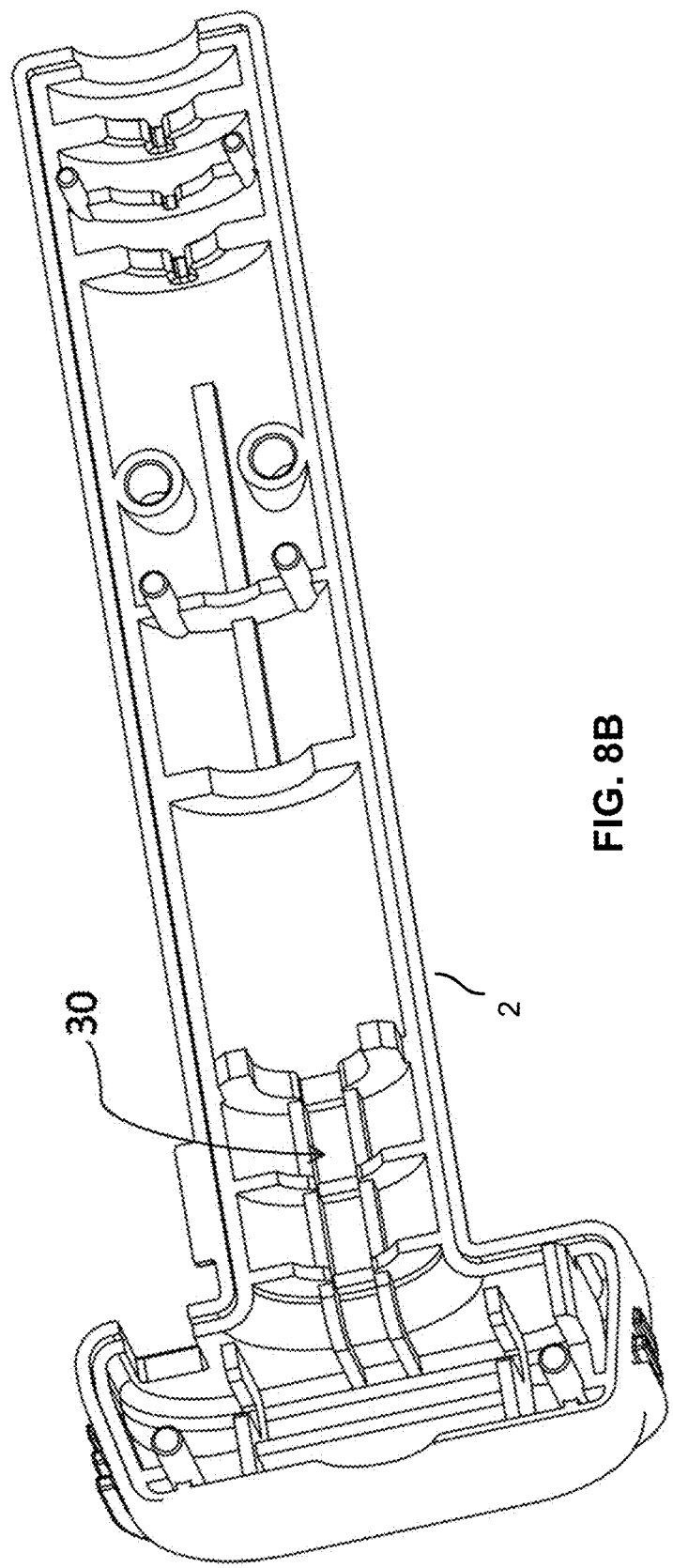
FIG. 8B is a three-dimensional illustration of the push member with the first set of sliding grooves shown in FIG. 8A.

Sliding grooves are provided to facilitate the sliding of components and also control the amount and direction of sliding. FIG. 8A is a schematic diagram of the interior of an embodiment of a push member with a first set of sliding grooves. The position of the sliding grooves 30 on the interior of push member 2 is shown. In various embodiments, the push member 2 and the sliding grooves can be formed using injection molding, machining, or any other appropriate techniques. The interior of push member 2 is formed with a first set of sliding grooves 30, which is adapted to first slider 18 on the pull rod 1 (shown in FIGS. 1A-1D). As discussed above, when the device is triggered, the first spring mechanism 12 is used to eject the pull rod 1. The coupling and cooperation of the sliding groove 30 and first slider 18 enables the pull rod 1 to slide inside the push member 2 in the forward direction without rotating. FIG. 8B is a three-dimensional illustration of the push member with the first set of sliding grooves shown in FIG. 8A.

Figure 9A:
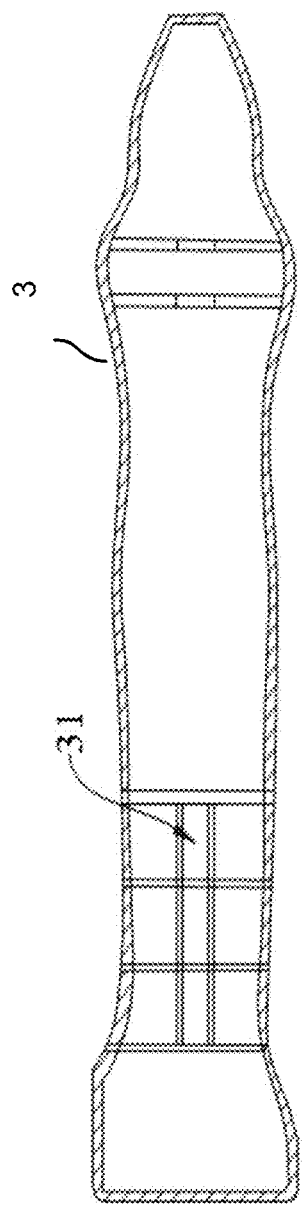
FIG. 9A is a schematic diagram of an embodiment of an operating handle that includes a second set of sliding grooves.
Figure 9B:
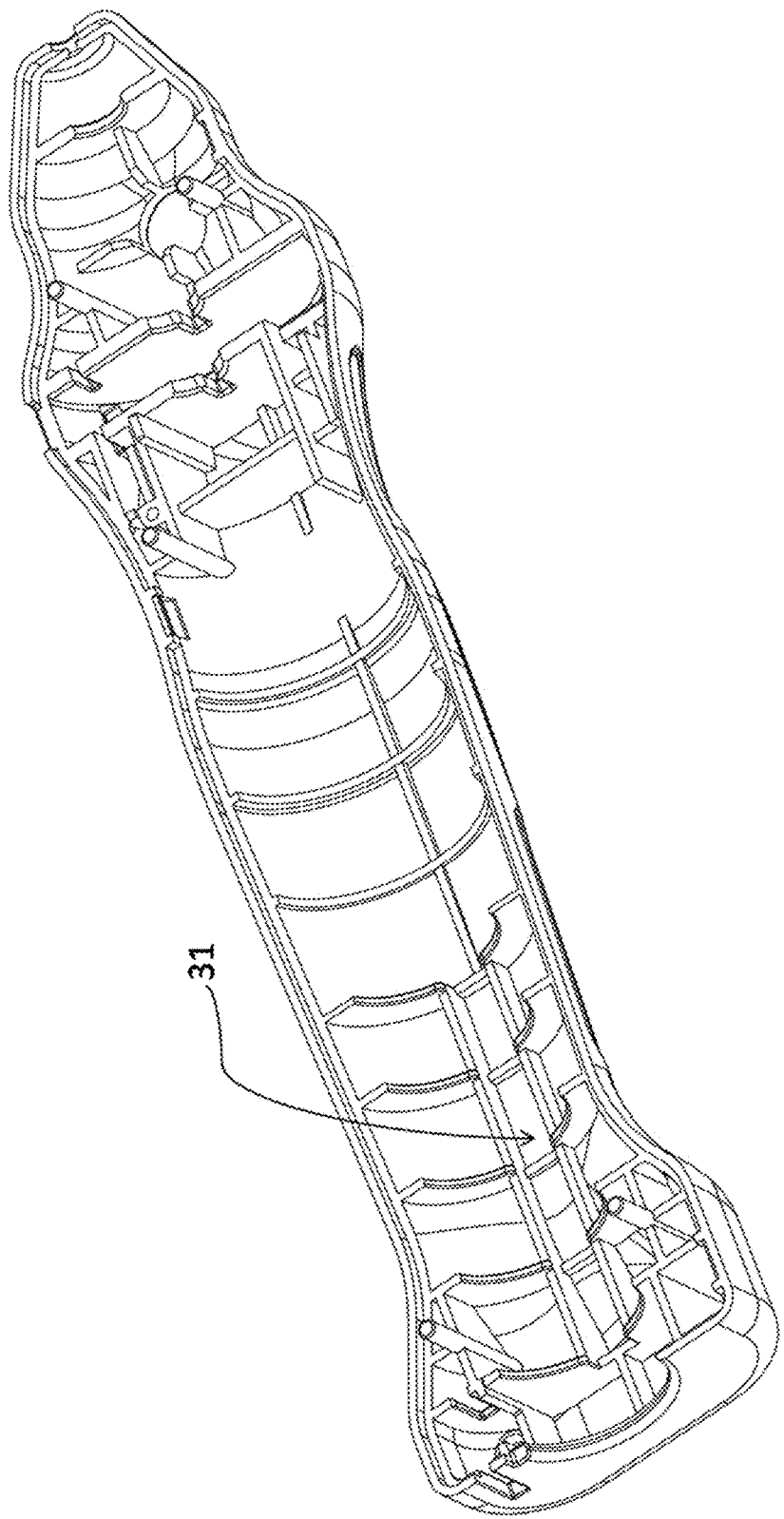
FIG. 9B is a three-dimensional illustration of the operating handle with the second set of sliding grooves shown in FIG. 9A.

FIG. 9A is a schematic diagram of an embodiment of an operating handle that includes a second set of sliding grooves. The second set of sliding grooves 31 is formed on the inside of handle casing 3. The position of the sliding grooves 31 on the interior of handle casing 3 is shown. In various embodiments, handle casing 3 and the sliding grooves are formed using injection molding, machining, or any other appropriate techniques. The interior handle 3 is formed with a second set of sliding grooves 31, which is adapted to second slider 32 on the push member 2. FIG. 9B is a three-dimensional illustration of the operating handle with the second set of sliding grooves shown in FIG. 9A.

Figure 10:
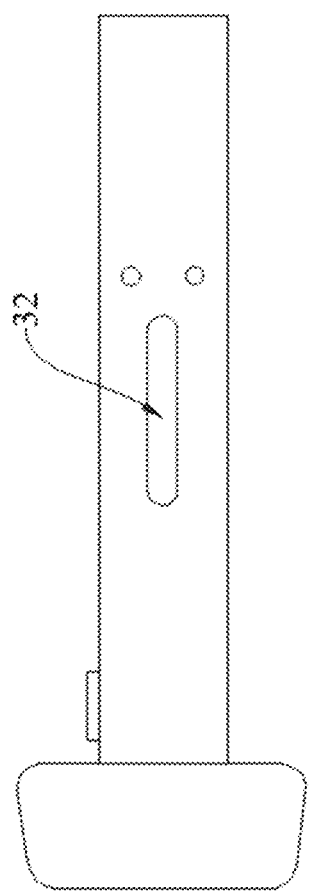
FIG. 10 is a schematic diagram of an embodiment of a push member with a second slider.
Figure 11:
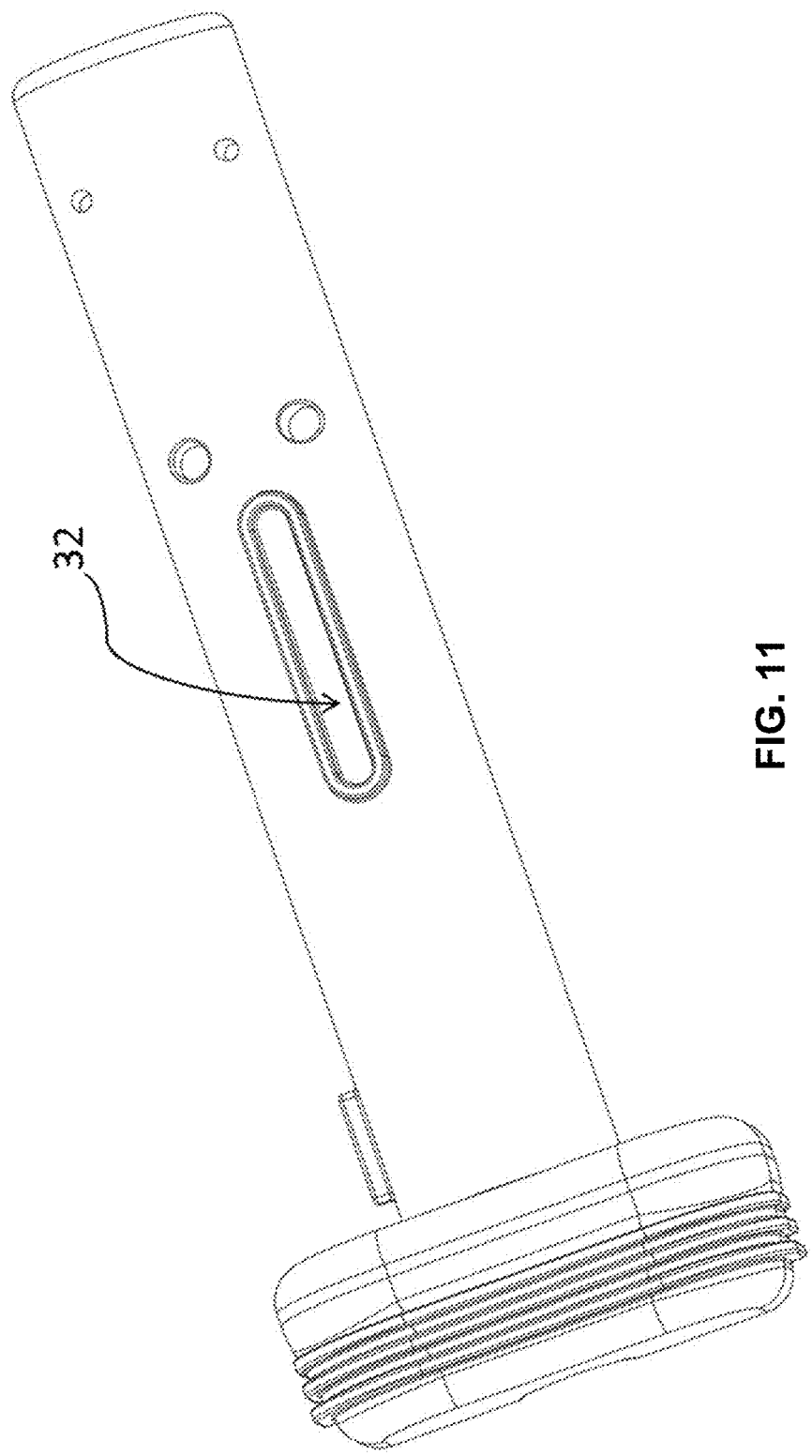
FIG. 11 is a three-dimensional illustration of the push member with the second slider of FIG. 10.

FIG. 10 is a schematic diagram of an embodiment of a push member with a second slider. As shown, second slider 32 is formed on the exterior of push member 2. The second slider 32 is adapted to engage the second set of sliding grooves 31 on the handle casing 3 (shown in FIGS. 9A and 9B). When the device is triggered, the second spring mechanism 13 is used for ejecting push member 2. The coupling and cooperation of the sliding groove 31 and second slider 32 allows the push member 2 to slide inside the handle in the forward direction without rotating. FIG. 11 is a three-dimensional illustration of the push member with the second slider of FIG. 10.

Figure 12A:
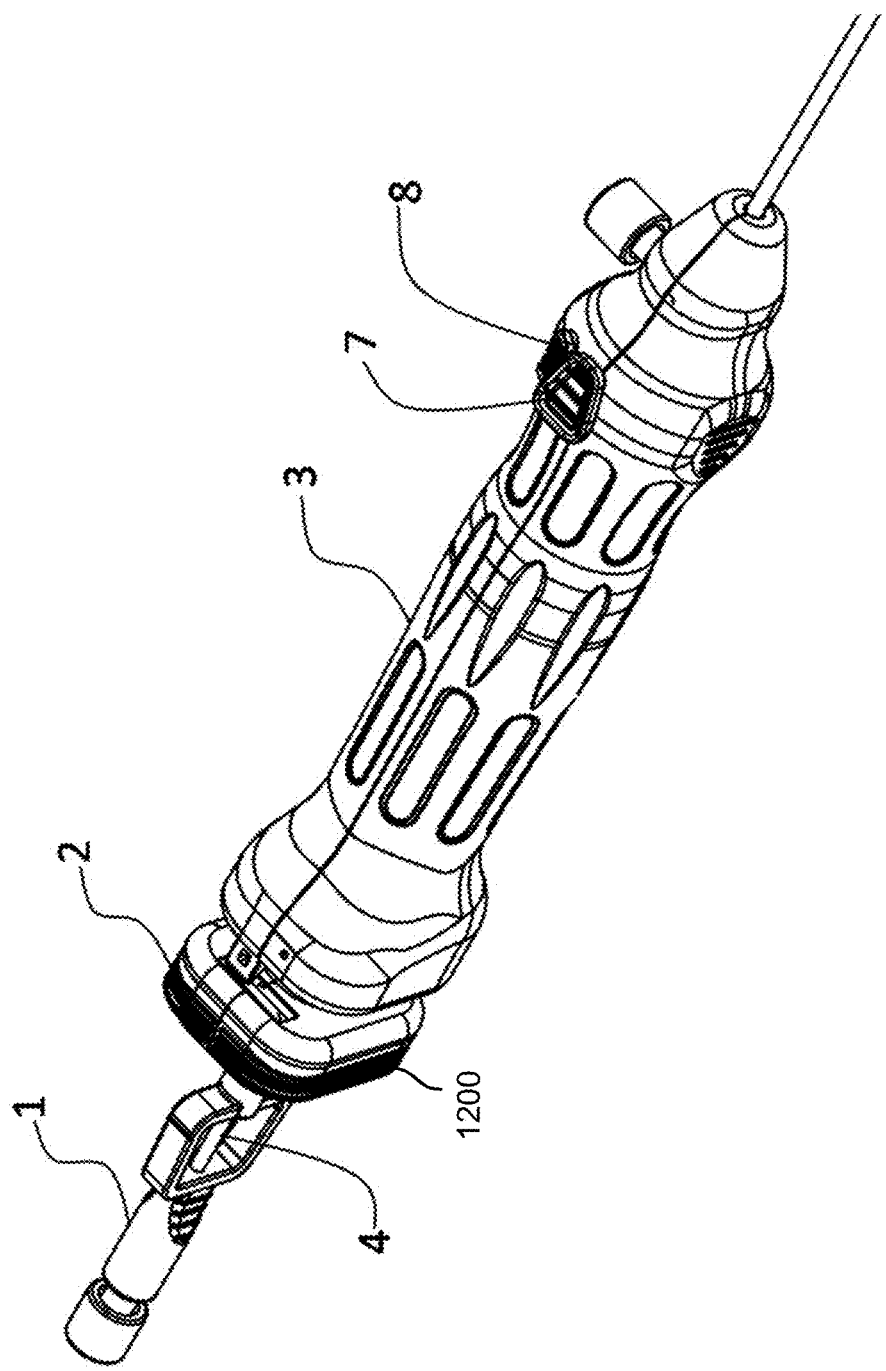
FIGS. 12A and 12B are perspective views of embodiments of the operating handle.
Figure 12B:
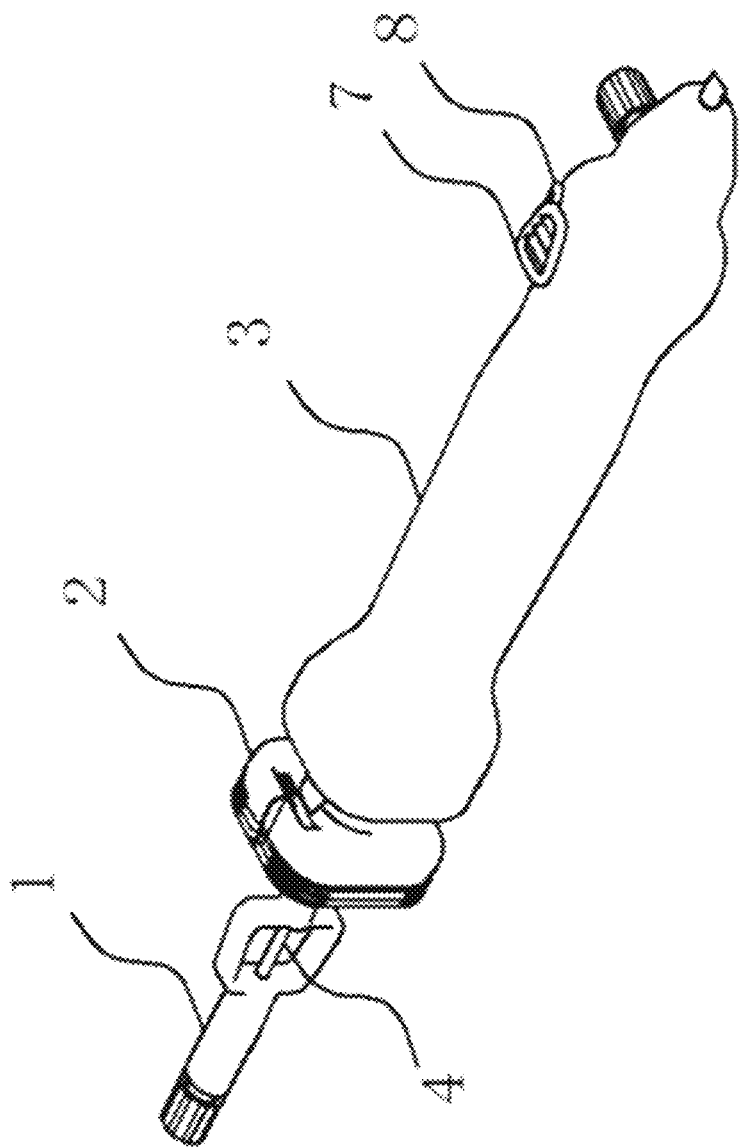

FIGS. 12A and 12B are perspective views of embodiments of the operating handle. In these figures, a housing structure 1200 is provided on the left side of the push member 2. In this case, the housing structure is square, thus it is also sometimes referred to as a square structure. Referring to FIG. 1A, the snapping member 5 is housed inside the housing structure and the snapping member 5 can move up and down along a sliding groove in the housing structure. A spring 42 is provided below the snapping member 5 to lock the pull rod 1 in place before triggering, and unlock the pull rod 1 when the device is triggered.

FIG. 1D is a diagram illustrating the state of system 100 after it has been triggered. After release button 7 is pushed and the device is triggered, the spring mechanisms 13 become expanded, ejecting pull rod 1 and push member 2 in the forward direction, thereby sending forward a pushing tube 11 and a delivery needle 10, as well as the repair component 21 stored therein (shown in FIG. 3). To accomplish this, in some embodiments, release button 7 has a C-shaped cross sectional area (in the Y-Z plane). Other shapes including an opening can be used. Prior to the device being triggered, the L-shaped rod 43 is pressed against the bottom part of release button 7. When release button 7 is pushed down at triggering time, the open part of the C shape drops down to where the L-shaped rod 43 is, and the expansive force of spring mechanism 13 pushes the L-shaped rod 43 into the open part of the C shape, causing both the spring mechanism 13 and the L-shaped rod 43 to shift in the forward direction, thus ejecting push member 2 in the forward direction. The pushing member 2 actuates the delivery needle 10 by pushing it forward and causing the delivery needle to pierce through the leaflet.

Further, on the interior of the handle casing 3, there is a second set of sliding grooves 31 (shown in FIGS. 9A and 9B). The second set of sliding grooves 31 is adapted to the second slider 32 on the push member 2. Together, the sliding grooves 31 and the second slider 32 allow the push member 2 to slide. When the device is initially set up, the push member 2 is pulled out, and the sliding member 6 is placed in a release position. When the device is triggered, the push member 2 is ejected forward under the action of the second spring mechanism 13. As a result, the sliding member 6 and the snapping member 5 come into contact, and the snapping member 5 is pushed downward by sliding member 6, causing the catch 40 on pull rod 1 to be released, thereby unlocking the pull rod 1. The expansive force of spring mechanism 12 (which has been under compression since the initial setup) ejects the pull rod 1 forward, which in turn pushes the pushing tube 11 forward. As the pushing tube 11 advances, it releases the repair component. Specifically, it pushes the anchor 211 through the hole in the leaflet made by the delivery needle and implants the anchor 211 at the desired location.

FIG. 7 is a schematic diagram showing the end portion of an embodiment of a device. As shown, the end of the pull rod 1 is connected with an evacuation connector 17 configured to extract air before the device enters the heart. In some embodiments, the evacuation connector 17 is implemented as a Luer connector.

The end of pull rod 1 further includes a stretching device comprising a wire clip 28 and a spring 29. The wire clip 28 is connected to the connection wire of the repair component 21, and the spring 29 is normally compressed. The stretching device is configured to stretch the connection wire and hold it under tension.

The tubular structure 4 (which can be made of polymer such as plastic) is sealed to prevent blood leakage. It also surrounds and protects the connection wire 212. After the anchor is deployed, the surgeon cuts the tubular structure and the connection wire inside it at a location such as 1000 to sever the connection wire and disengage the anchor from the delivery device. The anchor and the connection wire form an artificial chordae. The stretching device provided in the operating handle can automatically stretch the artificial chordae into a T-shaped structure after the artificial chordae is released, avoiding the artificial chordae remaining linearly shaped and easily disengaging from the valve leaflet after ejection.

The system for repairing valve leaflets in minimally invasive surgery provided in the present disclosure can be operated easily, and can realize release and repair operations by a linkage release operation which, in response to a single trigger (e.g., release button 7 being pressed), performs multiple actions including actuating the delivery needle and releasing the repair component. The overall system reduces operation difficulty and patient pain in the surgery. The surgery can be completed on a beating heart without bypass, and the surgery can accurately repair the function of the valve leaflet by means of the navigation function of modern imaging apparatus, such as ultrasonic apparatus, thoracoscopic apparatus, and laparoscopic apparatus.

The valve leaflet repair system of the present disclosure is suitable for the repairing of the valve leaflet in minimally invasive surgery. The system is easy to operate and can finish release and repair operations in response to a single trigger, and at the same time can reduce operation difficulty, intensity, and patient pain in the surgery, thereby improving the successful rate of the surgery.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for repairing a valve leaflet in minimally invasive surgery, comprising:
   a delivery device comprising:
      an operating handle;
      an outer delivery tube coupled to the operating handle;
      a delivery needle coupled to the operating handle; and
      a pushing tube coupled to the operating handle; and
      a repair component comprising an anchor and a connection wire; wherein:
   the operating handle comprises: a pull rod, a push member, a handle casing;
   the pull rod is connected to the pushing tube;
   the push member is fitted outside the pull rod;
   the push member is connected to the delivery needle;
   the handle casing is fitted outside the push member;
   the handle casing is connected to the outer delivery tube;

the outer delivery tube is fitted outside the delivery needle;

the pushing tube is located inside the delivery needle; and the delivery device is configured to, in response to being triggered, actuate the delivery needle and release the repair component.

2. The system as recited in claim 1, further comprising a positioning tube fitted outside the outer delivery tube.

3. The system as recited in claim 1, further comprising a positioning tube fitted outside the outer delivery tube, wherein the positioning tube is held in place by an outer tube clamp.

4. The system as recited in claim 1, further comprising a positioning tube fitted outside the outer delivery tube, and wherein the positioning tube is made of polymer.

5. The system as recited in claim 1, wherein the pull rod is driven by a spring mechanism.

6. The system as recited in claim 1, wherein the repair component is initially stored inside the delivery needle, and in response to the delivery device being triggered, the pushing tube is configured to release the repair component from inside the delivery needle.

7. The system as recited in claim 1, wherein the pull rod is connected with a tubular structure configured to stop blood leakage.

8. The system as recited in claim 1, wherein the pull rod is connected with a tubular structure that surrounds and protects the connection wire.

9. The system as recited in claim 1, wherein the pull rod is connected with a tubular structure that surrounds and protects the connection wire, and wherein the tubular structure and the connection wire are configured to be severed after the repair component is released.

10. The system as recited in claim 1, further comprising a spring mechanism that is located between the pull rod and the push member.

11. The system as recited in claim 1, further comprising a snapping member inside the push member, wherein the snapping member is configured to restrict the pull rod before the delivery device is triggered.

12. The system as recited in claim 1, further comprising:
a sliding member formed on the handle casing; and
a snapping member located in the push member; wherein the pull rod, the sliding member, and the snapping member are configured such that, when the pull rod is pulled out, the sliding member is placed in a release position, and the pull rod is locked by the snapping member.

13. The system as recited in claim 12, wherein the pull rod, the sliding member, and the snapping member are configured such that, in response to the device being triggered, the push member is ejected, and the sliding member and snapping member are configured to come into contact to cause the pull rod to be ejected.

14. The system as recited in claim 1, further comprising a release button configured to, in response to being pushed, cause the push member to be ejected.

15. The system as recited in claim 14, further comprising a safety button configured to prevent accidental triggering of the release button.

16. The system as recited in claim 1, wherein the anchor is configured to be attached to the valve leaflet.

17. The system as recited in claim 1, wherein the anchor is made of a metal or polymer material.

18. The system as recited in claim 1, wherein the connection wire is connected to the anchor, and the connection wire is made of a polymer material.

19. The system as recited in claim 1, wherein the outer delivery tube, the delivery needle, and the pushing tube form a three-layered structure.

20. The system as recited in claim 1, wherein the push member is fitted outside the pull rod, and the handle casing is fitted outside the push member.

21. The system as recited in claim 1, wherein:
the operating handle is provided with a first tube seat, a second tube seat and a third tube seat;
the pull rod is connected to the first tube seat;
the push member is connected to the second tube seat; and
the handle casing is connected to the third tube seat.

22. The system as recited in claim 21, wherein:
one end of the pushing tube is connected to the first tube seat, and the other end of the pushing tube passes through the center of the second tube seat;
one end of the delivery needle is connected to the second tube seat, and the other end of the delivery needle passes through the center of the third tube seat;
one end of the outer delivery tube is connected to the third tube seat; and
the anchor is connected to the connection wire.

23. The system as recited in claim 21, wherein:
the first tube seat is provided with a first engaging groove, the pushing tube is provided with a first engaging piece, and the first engaging groove fits with the first engaging piece;
the second tube seat is provided with a second engaging groove, the delivery needle is provided with a second engaging piece, and the second engaging groove fits with the second engaging piece; and
the third tube seat is provided with a third engaging groove, the outer delivery tube is provided with a third engaging piece, and the third engaging groove fits with the third engaging piece.

24. The system as recited in claim 1, wherein the operating handle includes:
a first spring mechanism located on the outside of the pull rod and the inside of the push member, configured to drive the pull rod when the delivery device is triggered; and
a second spring mechanism located on the outside of the push member and the inside of the handle casing, configured to drive the push member when the delivery device is triggered.

25. The system as recited in claim 1, wherein the pull rod is connected with an evacuation connector.

26. The system as recited in claim 1, wherein the pull rod is connected to a stretching device configured to hold the connection wire under tension.

27. The system as recited in claim 1, wherein:
the pull rod encloses a tubular structure that surrounds the connection wire; and
the tubular structure, the connection wire, and the anchor are configured such that, when the tubular structure and the connection wire within the tubular structure are cut, the anchor is disengaged from the delivery device.

28. The system as recited in claim 1, wherein:
a first set of sliding grooves is formed on the interior of the push member;
a first slider is formed on the exterior of the push member; and
the first set of sliding grooves and the first slider are configured to be adapted and to allow the pull rod to slide.

29. The system as recited in claim 1, wherein:
the push member is coupled to a housing structure;

a snapping member is provided in the housing structure;
a spring is provided to one end of the snapping member; and
the snapping member is configured to lock or unlock the pull rod under the control of the spring.

30. The system as recited in claim 1, wherein:
a second set of sliding grooves is formed on the interior of the handle casing;
a second slider is formed on the exterior of the push member; and
the second set of sliding grooves and the second slider are configured to be adapted to each other and to allow the push member to slide.

31. The system as recited in claim 1, wherein the handle casing further includes:
a safety button;
a spring coupled to the safety button; and wherein
the safety button is configured to lock or unlock a release button under action of the spring.

32. The system of claim 31, wherein the handle casing further includes a safety button reset hole, configured to reset the safety button after the safety button is unlocked.

* * * * *

UNITED STATES PATENT AND TRADEMARK OFFICE
CERTIFICATE OF CORRECTION

| | |
|---|---|
| PATENT NO. | : 11,678,984 B2 |
| APPLICATION NO. | : 16/852006 |
| DATED | : June 20, 2023 |
| INVENTOR(S) | : Qingliang Zhou et al. |

It is certified that error appears in the above-identified patent and that said Letters Patent is hereby corrected as shown below:

In the Specification

In Column 4, Line(s) 49 & 50, delete:
"the system shown in
FIG. 1A."
And insert:
--the system shown in FIG. 1A.--, therefor.

Signed and Sealed this
Seventh Day of November, 2023

Katherine Kelly Vidal
*Director of the United States Patent and Trademark Office*